United States Patent [19]

Hayes et al.

[11] Patent Number: 4,623,747

[45] Date of Patent: Nov. 18, 1986

[54] TERPENE DIESTERS AND PROCESS FOR PREPARING THE SAME

[75] Inventors: Kathryn S. Hayes, Norristown, Pa.; Jerome R. Olechowski, Lawrenceville, N.J.

[73] Assignee: Union Camp Corporation, Wayne, N.J.

[21] Appl. No.: 733,256

[22] Filed: May 13, 1985

[51] Int. Cl.$^4$ .................. C07C 67/313; C07C 69/602
[52] U.S. Cl. ..................................... 560/190; 562/595
[58] Field of Search ........................ 560/190; 562/595

[56] References Cited

U.S. PATENT DOCUMENTS

| | | | |
|---|---|---|---|
| 2,601,224 | 6/1952 | Roedel | 560/190 |
| 2,757,192 | 7/1956 | Jenner | 562/595 X |
| 3,984,462 | 10/1976 | Tsutsumi et al. | 560/190 |

*Primary Examiner*—Natalie Trousof
*Assistant Examiner*—Vera C. Clarke
*Attorney, Agent, or Firm*—Kane, Dalsimer, Kane, Sullivan and Kurucz

[57] ABSTRACT

A process for producing long-chained diesters of $C_{22}$ and $C_{32}$ diacids. The process comprises the steps of reacting cyclohexanone with an alcohol of 1–6 carbon atoms and hydrogen peroxide in the presence of an acid catalyst and water at a temperature below the boiling point of the alcohol. Methoxycyclohexyl hydroperoxide is thus produced and reacted with a terpene diene in the presence of a transition metal salt in a nitrogen atmosphere to produce long-chained diesters of $C_{22}$ and $C_{32}$ diacids. These long-chained diesters are then separated from the reaction mixture.

14 Claims, No Drawings

TERPENE DIESTERS AND PROCESS FOR PREPARING THE SAME

BACKGROUND OF THE INVENTION

1. Field of the Invention

The invention relates to novel $C_{24}$ and $C_{34}$ diesters and the method of their preparation.

2. Brief Description of the Prior Art

It has been known for some time that aliphatic aldehydes and ketones react with hydrogen peroxide to form hydroperoxide compounds of the type RCHOH(OOH). The hydroperoxide formed from cyclohexanone and hydrogen peroxide has been shown to have the simple structure:

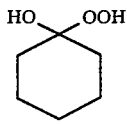
(I)

and also the structure:

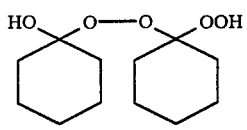
(II)

which may break down in solution to give cyclohexanone and 1,1-dihydroperoxycyclohexanone. It has been shown that the solid peroxide of structure (II) when shaken with an aqueous solution of ferrous sulfate yields mainly hexanoic and 1,12-dodecanedioic acids and cyclohexanone.

The reaction of ferrous salts with peroxides derived from cyclic ketones has occasioned considerable interest, largely the result of the formation of open chain products, particularly those having double the number of carbon atoms present in the original ketones: such products bear close resemblance to those obtained from 1-hydroperoxy-1-alkylcycloalkanones. Replacement of ferrous sulfate with ferrous chloride leads to a sharp decrease in the yield of $C_{12}$ diacid. This result is not surprising in view of French Patent No. 1,152,642, which claims that good yields of 6-chlorohexanoic acid may be produced under these conditions. Conditions which lead to decreased yields include high temperatures, poor mixing and the use of reduced proportions or concentrations of hydrogen peroxide.

As described in U.S. Pat. No. 2,601,223, Brown has achieved high conversions of the $C_{12}$ diacid using methanol solutions of the peroxides, derived from the oxidation of cyclohexanol. Cyclic ketones other than cyclohexanone have been found to react in a similar manner, although yields of corresponding dicarboxyclic acids have been found to be generally lower: 2-chloro-1-hydroperoxycyclohexanol gave dichlorododecanedioic acid; cyclopentanone, sebacic acid, and 4-methylcyclohexanone give 4,9-dimethyl dodecanedioic acid.

U.S. Pat. No. 2,757,192 has disclosed that the introduction of conjugated dienes such as butadiene, isoprene, and chloroprene into the reaction mixture of ketone and hydrogen peroxide leads to the formation of long chain unsaturated dicarboxylic acids, with the addition of butadiene giving rise to the $C_{20}$ acids including:

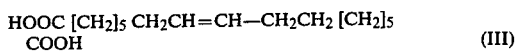
(III)

It has also been shown that the conjugated dienes may be replaced by dimethyl maleate giving rise to a hexaester formed by dimerization of the radical:

(IV)

(See *J. Org. Chem.*, 23, 1066 (1958)).

U.S. Pat. No. 3,984,462 describes the process for producing dodecanedioic acid dimethyl ester. This process is a modification of the above described technology by substituting methanol as the solvent. The use of methanol as solvent for higher conversion to the $C_{12}$ acid has been reported by Brown in *J.Am. Chem. Soc.*, 77, 1756 (1955). The process comprises the reaction of cyclohexanone with methanol and hydrogen peroxide in the presence of an acid catalyst to produce methoxycyclohexylhydroperoxide and subsequent reaction with ferrous sulfate. The methyl esters produced may be separated by distillation and subsequently saponified to recover the corresponding diacids which are then separated by fractional crystallization of the linear and branched products.

Japanese Patents Nos. 78 59,618, and 78 63,309 describe a process where butadiene is added in the second step to produce $C_{20}$ dimethyl esters.

SUMMARY OF THE INVENTION

The invention comprises select diesters having 24 or 34 carbon atoms in the carboxylate, inclusive. The invention also comprises a process for their preparation, comprising the steps of reacting cyclohexanone with methanol and hydrogen peroxide in the presence of an acid catalyst and water. This reaction takes placed at a temperature below the boiling point of the alcohol to produce methoxycyclohexyl hydroperoxide. The methoxycyclohexyl hydroperoxide is then reacted with a terpene triene or diene in the presence of a ferrous salt under an inert atmosphere. Long-chained diesters are thus produced.

The diesters of the invention are useful intermediates for the preparation of polyester, polyamide, poly(esteramide) resins which are useful as hot-melt adhesives, in flexographic inks, and as epoxy curing agents, and preparation of esters as lubricants and amidoamines as corrosion inhibitors.

DETAILED DESCRIPTION OF THE INVENTION

To practice the process of this invention, cyclohexanone, a $C_1$-$C_6$ alcohol, and hydrogen peroxide are first reacted in the presence of an acid catalyst and water.

It is especially critical to use about 15 to 26 moles of an alcohol of 1-6 carbon atoms per mole of cyclohexanone with the preferred alcohol being methanol. If the amount of methanol is less than about 15 moles, methoxycyclohexyl hydroperoxide is obtained in a low yield and as a result the diesters subsequently produced will be obtained only in a low yield. Preferably about 18 to 30 moles of methanol are used per mole of cyclohexanone. The amount of hydrogen peroxide used in the present process is about 0.5 to 1.5 moles, preferably about 0.7 to 1.2 moles per mole of cyclohexanone.

Representative of the acid catalyst are sulfuric acid, hydrochloric acid, nitric acid, phosphoric acid, and like inorganic mineral acids. The acid catalyst is used in a catalytic proportion, i.e.; in an amount of at least 0.01 mole preferably about 0.02 to 0.05 moles, per mole of cyclohexanone.

The amount of water to be used is at least 2 moles, preferably 3 to 6 moles, per mole of cyclohexanone. It is preferred to use water mixed with hydrogen peroxide or methanol. The reaction can be conducted below the boiling point of methanol, preferably at $-20°$ C. to $60°$ C. The reaction is allowed to proceed until cyclohexanone is substantially converted to methoxycyclohexyl hydroperoxide.

The resulting methoxycyclohexyl hydroperoxide is then subjected to a subsequent reaction without being separated from the reaction mixture. The second reaction is carried out in the presence of a metal salt that decomposes peroxides such as ferrous sulfate and cuprous chloride, at least 2 moles of the desired terpene triene or diene per mole of the starting cyclohexanone, and at least about 25 moles of methanol per mole of the starting cyclohexanone. If the amount of unreacted methanol from the first step in the process, is more than about 25 moles per mole of the starting cyclohexanone, there is no need to add fresh methanol. However it can be added as desired.

Suitable for use as the metal salts are any of various known ferrous salts such as for example, ferrous sulfate, ammonium ferrous sulfate, ferrous chloride, copper salts, such as for example cuprous sulfate, cuprous chloride, cuprous nitrate and other transition metals. The metal salt is used in near stoichiometric amount, preferably 0.5 to 5 moles per mole of the starting cyclohexanone, the most preferable amount being in the range of 0.7 to 2 moles per mole of the starting cyclohexanone.

Suitable for use as the unsaturated terpenes are myrcene, dihydroallo-ocimene, ocimene, allo-ocimene, α-Terpinene, and β-Phellandrene. Preferred are the terpene trienes myrcene, allo-ocimene and ocimene. The terpene trienes are used preferably 1 to 4 moles per mole of the starting cyclohexanone, the most preferable amount being in the range of 1.5 to 3 moles per mole of the starting cyclohexanone.

The reaction mixture containing methoxycyclohexyl hydroperoxide, ferrous salt, the desired unsaturated terpene, and methanol can be mixed together in any desired order.

The long-chained diesters obtained can be easily separated from the resulting reaction mixture. For example the reaction mixture is distilled to recover methanol (approximately 80%) and the residue is left to stand. Upon cooling, the residue separates into two layers, an upper layer which contains the desired esters and a lower layer of ferric sulfate solution. The upper layer is separated by washing with water, and then drying over anhydrous sodium sulfate.

The following Examples describe the manner and the process of making and using the invention and set forth the best mode contemplated by the inventor of carrying out the invention but are not to be construed as limiting.

EXAMPLE 1

Preparation of diesters of the formula

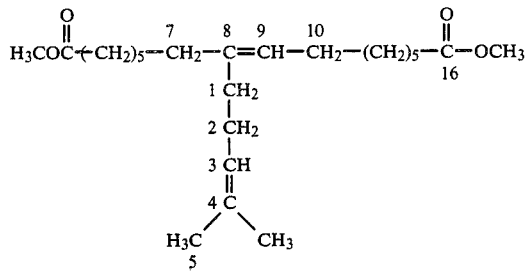

and

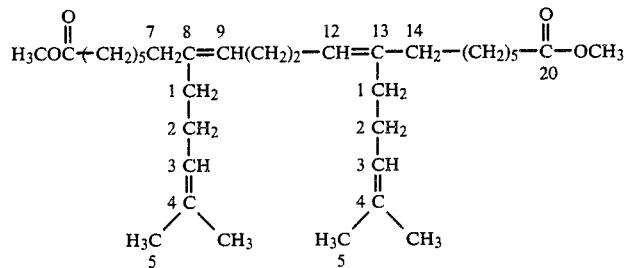

In Flask A a solution of methoxycyclohexylhydroperoxide was prepared by addition of 30 wt % hydrogen peroxide to a solution of cyclohexanone in methanol containing a catalytic amount of concentrated $H_2SO_4$. The reaction was carried out at approximately $10°$ C. In Flask B, under a nitrogen atmosphere a mixture of ferrous sulfate, myrcene, and methanol was prepared. The absence of air in the Flask could readily be determined by the white color of the mixture. The contents of Flask A were added to Flask B at a rate so as to maintain the temperature between $25°-30°$ C. When all the methoxycyclohexyhydroperoxide solution had been added, the mixture was stirred under nitrogen for an additional hour. Then approximately 80% of the methanol utilized as solvent was distilled from the mixture. Upon cooling, the system separated into two layers. The upper layer which contained the desired esters was separated, washed with water, dried over anhydrous sodium sulfate, and analyzed by liquid chromatography and gas chromatography, where possible. The LC analysis was performed on a 100A μ-spherogel size exclusion column with tetrahydrofuran as the solvent. Gas chromatography of the first fraction obtained in the distillation of the myrcene system showed only about 10 area percent of the $C_{12}$ dimethyl ester.

The product mixture is mixture of dimethyl 8-(4-methyl-3-pentenyl)-cis-8-hexadecene-1,16-dioate, dimethyl 8-(4-methyl-3-pentenyl)-trans-8-hexadecene-1,16-dioate, dimethyl 8,13-bis(4-methyl-3-pentenyl)-trans-8,12-eicosadiene-1,20-dioate, dimethyl 8,13-bis(4-methyl-3 pentenyl)-cis-8-trans-12-eicosadiene-1, 20-dioate, dimethyl 8,13-bis(4-methyl-3-pentenyl-trans-8-cis-12 eicosadiene-1,20-dioate, and dimethyl 8,13-bis(4-methyl-3-pentenyl)-trans-8,12 eicosadiene-1,20-dioate.

The process of example 1 was repeated except that alloocimene was used in place of myrcene. The long-chained $C_{22}$ diesters produced were dimethyl 7-(2-methyl-1-propenyl)-9,10-dimethyl-cis-8-hexadecene-1,10-dioate and dimethyl 7-(2-methyl-1-propenyl)-9,10-dimethyl-trans-8-hexadecene-1,16dioate. The long-chained $C_{32}$ diesters produced were dimethyl 7,14-bis(2-methyl-1-propenyl)-9,10,11,12-tetramethyl-cis-8, cis-12-eicosadiene-1,20-dioate, dimethyl 7,14-bis(2-methyl-1-propenyl)-9,10,11,12-tetramethyl-cis-8-trans-12-eicosadiene-1,20-dioate, dimethyl 7,14-bis(2-methyl-1-propenyl)-9, 10,11,12- tetramethyl-trans-8-cis-12-eicosadiene-1,20-dioate, and dimethyl 7,14-bis(2-methyl-1-propenyl)-9,10,11, 12- tetramethyl-trans-8-trans-12-eicosadiene-1,20-dioate.

EXAMPLE 2

Preparation of diesters of the formulae

EXAMPLE 3

Preparation of Diesters of the formulae

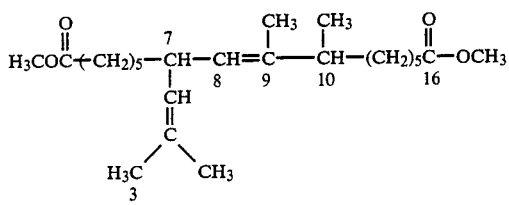

and

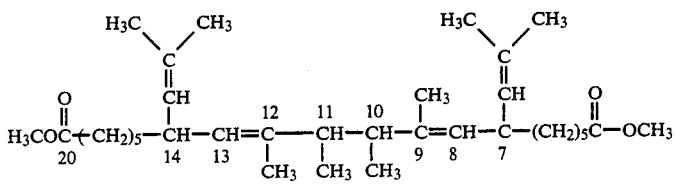

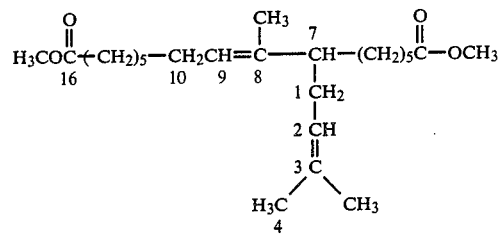

and

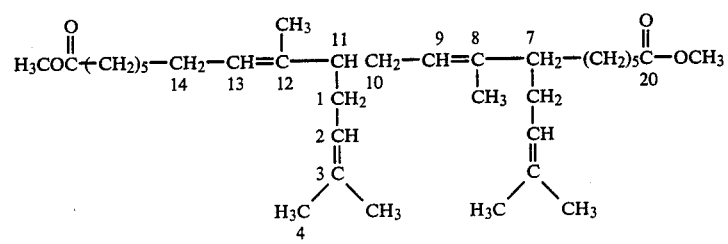

and

-continued

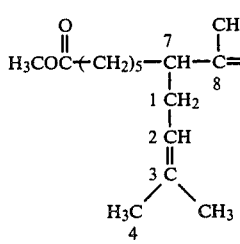 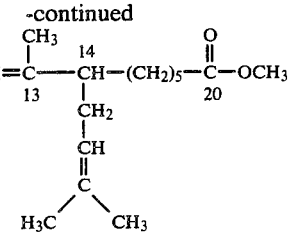

The process of example 1 was repeated except that ocimene was used in place of mycrene. The long-chained $C_{22}$ diester produced was dimethyl 7-(3-methyl-2-butenyl) 8-methyl-cis-8-hexadecene-1,16-dioate. The long-chained $C_{32}$ diesters produced were dimethyl 7,11-bis (3-methyl-2-butenyl)-8,12-dimethyl-trans-8-cis-12-eicosadiene-1,20-dioate, dimethyl 7,11-bis(3-methyl-2-butenyl)-8,12-dimethyl-cis-8-trans-12-eicosadiene-1,20-dioate, dimethyl 7,11-bis(3-methyl-2-butenyl)-8,12-dimethyl-cis-8-cis-12-eicosadiene-1,20-dioate, dimethyl 7,11-bis(3-methyl-2-butenyl)-8,12-dimethyl-trans-8-trans-12-eicosadiene-1,20-dioate, dimethyl 7,14-bis(3-methyl-2-butenyl)-8,13-dimethyl-trans-8-cis-12-eicosadiene-1, 20-dioate, dimethyl 7,14-bis(3-methyl-2-butenyl)-8,13-dimethyl-cis-8-cis-12-eicosadiene-1,20-dioate, dimethyl 7,14-bis(3-methyl-2-butenyl)-8,13-dimethyl- cis-8-trans-12-eicosadiene-1,20-dioate, dimethyl 7,14-bis (3-methyl-2-butenyl)-8,13-dimethyl-trans-8-trans-12-dimethyl-8,12-eicosadiene-1,20-dioate.

What is claimed:

1. The dimethylester of a $C_{22}$ diacid obtained from the double bond addition of two carbomethoxyhexyl radicals to an unsaturated terpene.

2. The dimethylester of claim 1 wherein said terpene is selected from the group consisting of myrcene, allo-ocimene and ocimene.

3. The dimethylester of claim 1 selected from the group consisting of dimethyl 8-(4-methyl-3-pentenyl)-8-hexadecene-1, 16-dioate, dimethyl 7-(2-methyl-1-propenyl)-9-10-dimethyl-8-hexadecene-1, 10-dioate and dimethyl 7-(3methyl-2-butenyl)-8-methyl-8-hexadecene-1, 16-dioate.

4. The dimethylester of a $C_{32}$ diacid obtained from the double bond addition of a carbomethoxylhexyl radicals to each of two molecules of an unsaturated terpene, which then couple.

5. The dimethylester of claim 4 wherein said terpenes are selected from the group consisting of myrcene, allo-ocimene and ocimene.

6. The dimethylester of claim 4 selected from the group consisting of dimethyl 8,13-bis(4-methyl-3-pentenyl)-8,12- eicosadiene-1,20-dioate, dimethyl 7,14-bis(2-methyl-1 -propenyl)-9,10,11,12-tetramethyl-8,12-eicosadiene-1,20-dioate, dimethyl 7,11-bis(3-methyl-2-butenyl)-8-12-dimethyl-8, 12-eicosadiene-1,20-dioate and dimethyl 7,14-bis(3-methyl-2- butenyl)-8,13-dimethyl-8,12-eicosadiene-1,20-dioate.

7. The process for producing dimethylesters of $C_{22}$ and $C_{32}$ diacids comprising; reacting cyclohexanone with methanol and hydrogen peroxide in the presence of an acid catalyst and water at a temperature below the boiling point of said methanol to produce methoxycyclohexyl hydroperoxide, then reacting said methoxycyclohexyl hydroperoxide with an unsaturated terpene triene in the presence of a transistion metal salt under an inert atmosphere, and separating the resulting dimethylesters from the reaction mixture.

8. The process for producing dimethylesters of $C_{22}$ and $C_{32}$ diacids according to claim 7 wherein said terpene triene is myrcene, and said $C_{22}$ dimethylester is dimethyl 8-(4-methyl-3-pentenyl)-8- hexadecene-1,16-dioate and the $C_{32}$ dimethylester is dimethyl 8,13-bis(4-methyl-3-pentenyl)-8-12eicosadiene 1,16-dioate, with both cis and trans isomers being formed.

9. The process of producing dimethylesters of $C_{22}$ and $C_{32}$ diacids according to claim 7 wherein said terpene triene is allo-ocimene, and said $C_{22}$ dimethylester is dimethyl 7-(2-methyl-1-propenyl)-9,10-dimethyl-8-hexadecane-1,16dioate and said $C_{32}$ dimethylester is dimethyl 7,14-bis(2-methyl-1-propenyl)-9,10,11,12-tetramethyl-8,12- eicosadiene-1,20-dioate.

10. The process for preparing dimethylesters of $C_{22}$ and $C_{32}$ diacids according to claim 7 wherein said terpene triene is ocimene and said $C_{22}$ dimethylester is dimethyl 7-(3-methyl-2-butenyl)-8-methyl-8-hexadecene-1, 6-dioate and said $C_{32}$ dimethylesters are dimethyl 7,11-bis(3-methyl-2-butenyl)-8,12-dimethyl-8,12-eicosadiene- -1,20-dioate and dimethyl 7,14-bis(3methyl-2-butenyl)-8,13-dimethyl-8, 12-eicosadiene-1,20-dioate.

11. The process according to claim 7 wherein said acid catalyst is $H_2SO_4$.

12. The process according to claim 7 wherein said transition metal salt is a ferrous salt.

13. The process according to claim 7 wherein said transition metal salt is a ferrous sulfate hexahydrate.

14. The process according to claim 7 wherein said transition metal salt is a cuprous salt.

* * * * *